US00PP35139P2

(12) United States Plant Patent
Elsworth

(10) Patent No.: US PP35,139 P2
(45) Date of Patent: Apr. 25, 2023

(54) ***AJUGA* PLANT NAMED 'NOBNIG'**

(50) Latin Name: *Ajuga tenorii*
Varietal Denomination: Nobnig

(71) Applicant: Kelly Elsworth, Portage, MI (US)

(72) Inventor: Kelly Elsworth, Portage, MI (US)

(73) Assignee: Christopher M. Hansen, Zeeland, MI (US)

( * ) Notice: Subject to any disclaimer, the term of this patent is extended or adjusted under 35 U.S.C. 154(b) by 0 days.

(21) Appl. No.: 17/687,345

(22) Filed: Mar. 4, 2022

(30) Foreign Application Priority Data

Dec. 23, 2021 (QZ) ..... PBR 20213440

(51) Int. Cl.
*A01H 5/02* (2018.01)
*A01H 6/50* (2018.01)

(52) U.S. Cl.
USPC ..... Plt./401

(58) Field of Classification Search
USPC ..... Plt./401
CPC ... A01H 5/12; A01H 5/02; A01H 5/00; A01H 6/50
See application file for complete search history.

(56) References Cited

U.S. PATENT DOCUMENTS

PP20,734 P2 * 2/2010 Saul ..... Plt./401

OTHER PUBLICATIONS

CPVO Register 4.2.27, retrieved on Aug. 9, 2022 at https://online.plantvarieties.eu/publicConsultationDetails?registerId=20213440&denomination=nobnig, 3 pp. (Year: 2022).*
Leo Berbee Young Plants 2021, retrieved on Aug. 9, 2022 at https://berbeeyoungplants.com/plants/Mast%20Perennials%202021.pdf, 2 pp. (Year: 2021).*
Mast Young Plants 2020, retrieved on Aug. 9, 2022 at http://www.mastyoungplants.com/myp-news/featheredfriends/, 5 pp. (Year: 2020).*
CPVO Register version 4.2.56 for *Ajuga* Nobnig, retrieved on Nov. 22, 2022 at https://online.plantvarieties.eu/publicConsultationDetails?registerId=20213440&denominati, 3 pp. (Year: 2022).*

* cited by examiner

*Primary Examiner* — June Hwu
(74) *Attorney, Agent, or Firm* — Penny J Aguirre

(57) ABSTRACT

A new cultivar of *Ajuga* plant named 'Nobnig' that is characterized by its foliage that is dark purple in color and remains dark and uniform in color throughout the cold winter months, its leaves that are glossy, its flowers that are blue in color, and its groundcover plant habit.

3 Drawing Sheets

Botanical classification: *Ajuga tenorii.*
Variety denomination: 'Nobnig'.

CROSS-REFERENCE TO RELATED APPLICATIONS

This application claims priority to European Community Plant Variety Office (CPVO) Plant Breeder's Rights Application No. 2021/3440 filed on Dec. 23, 2021, under 35 U.S.C. 119(f), the entire contents of which is incorporated by reference herein. This application is co-pending with a U.S. Plant Patent Application filed for a plant derived from the same breeding program that is entitled *Ajuga* Plant Named 'Fanfin' (U.S. Plant patent application Ser. No. 17/687,273).

BACKGROUND OF THE INVENTION

The present invention relates to a new and distinct cultivar of *Ajuga tenorii* and will be referred to hereafter by its cultivar name, 'Nobnig'. 'Nobnig' represents a new cultivar of *Ajuga*, an herbaceous perennial grown for landscape use.

The new Invention arose from an ongoing controlled breeding program in Hudsonville, Mich. The objective of the breeding program is to develop new cultivars of *Ajugas* with unique foliage coloration, different leaf sizes and strong clump forming growth habits.

The new cultivar arose from a controlled cross made in March of 2019 between *Ajuga tenorii* 'Chocolate Chip' (not patented) as both the female and male parents. The Inventor selected 'Nobnig' as a single unique plant from amongst the seedlings of the above cross in May of 2020.

Asexual propagation of the new cultivar was first accomplished by stem tip cuttings in June of 2020 in Hudsonville, Mich. Propagation by stem tip cuttings has determined the characteristics to be stable and reproduced true to type in successive generations.

SUMMARY OF THE INVENTION

The following traits have been repeatedly observed and are determined to be the characteristics of the new cultivar. These attributes in combination distinguish 'Nobnig' as a unique cultivar of *Ajuga*.

1. 'Nobnig' exhibits foliage that is dark purple in color and remains dark and uniform in color throughout the cold winter months.
2. 'Nobnig' exhibits leaves that are glossy.
3. 'Nobnig' exhibits flowers that are blue in color.
4. 'Nobnig' exhibits a groundcover plant habit.

The parent plant of 'Nobnig', 'Chocolate Chip', differs from 'Nobnig' in having foliage that is lighter purple and more green in color in cold winter months and leaves that are shorter in length. 'Nobnig' can be most closely compared to

*Ajuga tenorii* cultivar 'Mint Chip' (U.S. Plant Pat. No. 20,734) and *Ajuga* 'Fanfin'. 'Mint Chip' is similar to 'Nobnig' in having flowers that are blue in color and a dense groundcover growth habit. 'Mint Chip' differs from 'Nobnig' in having foliage that is green in color and leaves that are shorter in length. 'Fanfin' is similar to 'Nobnig' in having flowers that are blue in color, similar shaped leaves, and a dense groundcover growth habit. 'Fanfin' differs from 'Nobnig' in having tri-colored foliage and winter foliage that is copper-bronze in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but are not limited to website publications by Spring Hill Nursery, Romence Gardens, Bloomin Designs, Michigan Bulb, Winter Green House, Great Garden Plants, Wilson Bros Gardens, Mountain Crest Gardens, In the Country Garden and Gifts, WalMart, Garden Crossings, Garden Solutions Plants, Plant Central, Peace Tree Farm, Quality Cuttings, White House Plants, Millette Photo Media, Garden Center Ohio, Amazon, Evergreen Nursery Inc, Pinterest, Chicago Botanic, Emerisa, Creekside Gardens Inc, Phoenix Perennials, Earth, Baker Sacres Greenhouse, 2 Bing, You Tube, Houzz, George Weigel, Milled, Rideau Woodland Ramble, Gateway Gardens, Fermebedardblouin, Get Blooming, Green Profit, Express Seed, bhg, thursd, Preen, O Canada, Greenland Garden, Peconicrive Herb Farm, Barsons, svgplants, The Observer, Germania Seed, Windor Star, ehrnet, Multi Screen Site, degroots, Sherwoods Forests, Garden Works, Zyromski, and rslandscape design.

BRIEF DESCRIPTION OF THE DRAWINGS

The accompanying color photographs illustrate the overall appearance and distinct characteristics of the new *Ajuga* as grown in a greenhouse in Hudsonville, Mich.

The photograph in FIG. 1 provides a side view of a 6-month-old plant of 'Nobnig' as grown in a 1-quart container.

Figure 1:
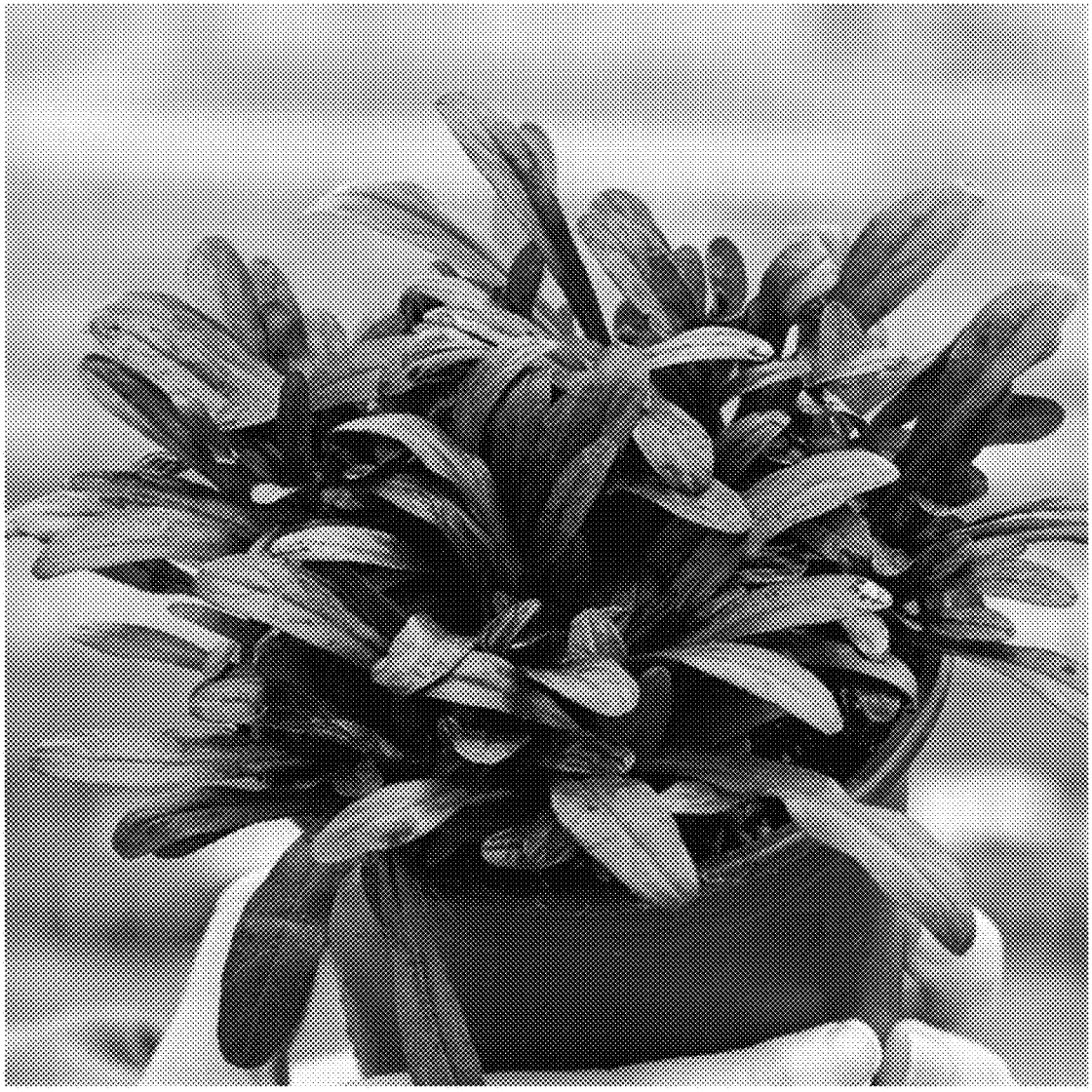
Figure 2:
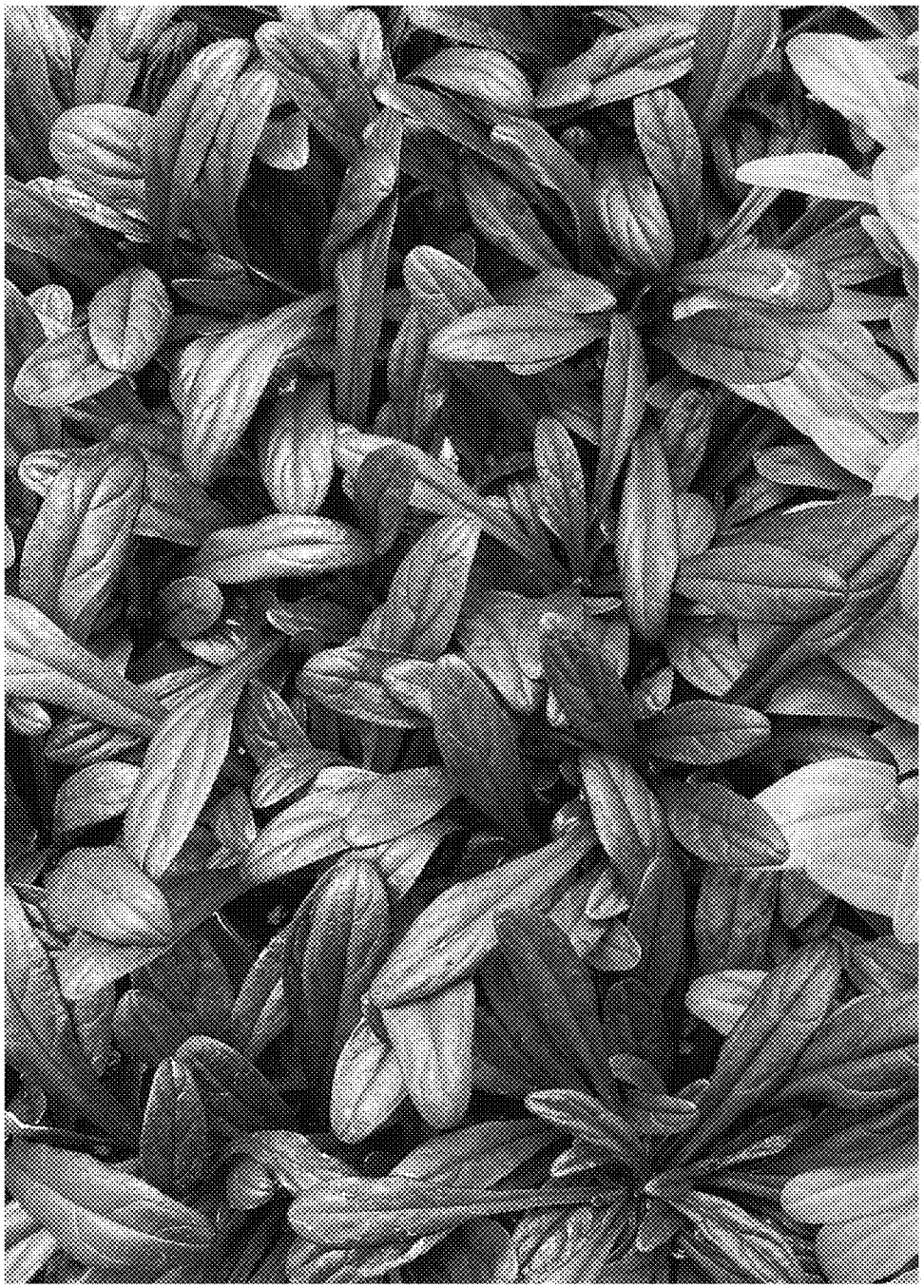

The photograph in FIG. 2 provides a close-up view of the foliage of 3-months-old plants of 'Nobnig' as grown in 50-cell plugs.

Figure 3:
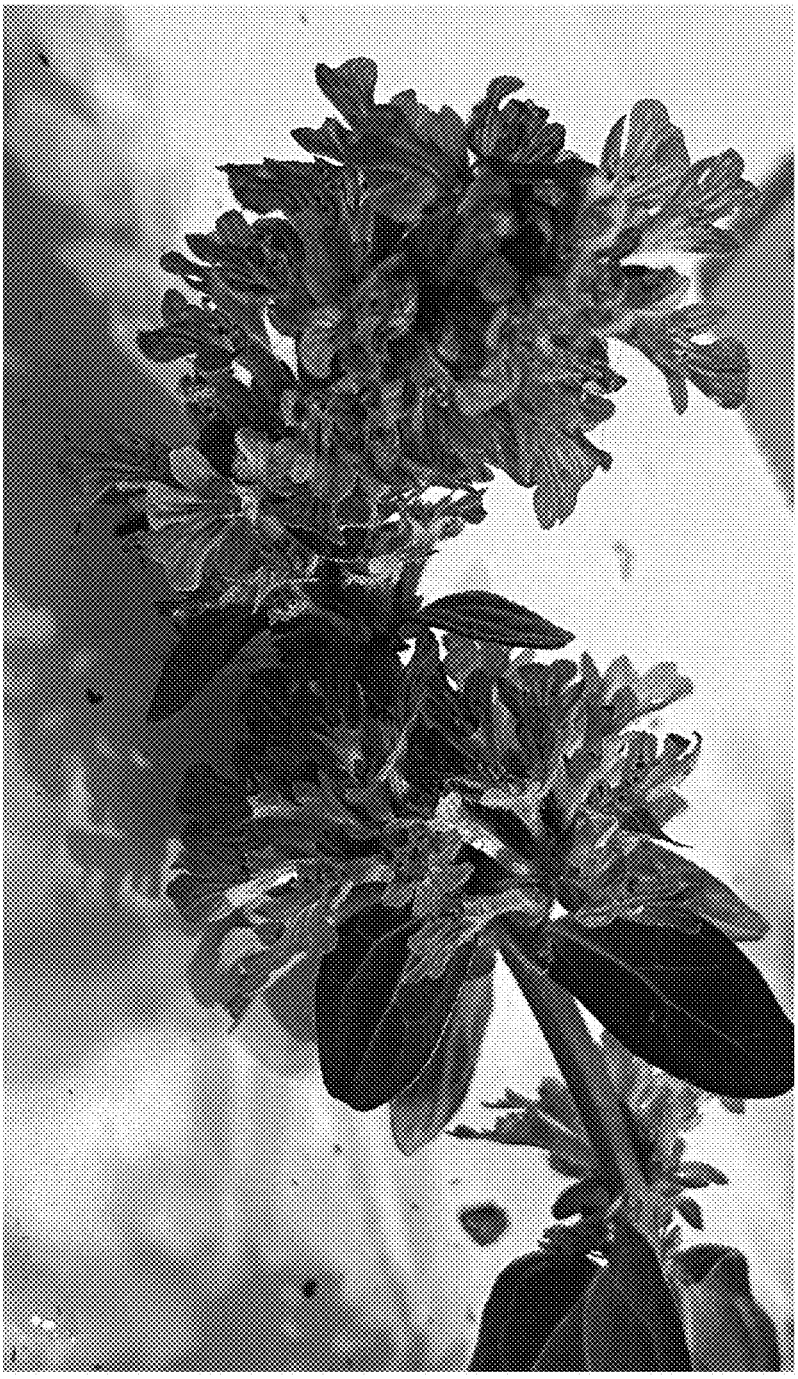

The photograph in FIG. 3 provides a view of an inflorescence of 'Nobnig' as grown as a 6-month-old-plant grown in a 1-qt container.

The colors in the photographs may differ slightly from the color values cited in the detailed botanical description, which accurately describe the colors of the new *Ajuga.*

DETAILED BOTANICAL DESCRIPTION

The following is a detailed description of the new cultivar as observed on 6-month-old plants as grown in a greenhouse in 4-inch containers in Hudsonville, Mich. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

Blooming period: 4 to 6 weeks commencing in late spring in Michigan.

Plant type: Herbaceous perennial.

Plant habit: Dense and rounded, groundcover, compact upright inflorescences.

Height and spread: 16 cm in height (soil level to top of floral plane), an average of 7 cm in height (soil level to top of foliar plane) and 13 cm in width, mature plant in the landscape reaches an average of 10 cm in height and 46 cm in spread.

Hardiness: At least in U.S.D.A. Zones 4 to 8.

Diseases and pests: Plants have been observed to be disease free, however no resistance to any specific diseases is known, no resistance or susceptibility to pests has been observed.

Root description: Fine and fibrous, a blend of 158A and NN155A in color.

Propagation type: Tip stem cuttings.

Root development: An unrooted stem cutting will fully root in a 50-cell plug in 8 weeks and a 50-cell plug will fully root in a 1-gallon container in 10 weeks.

Growth rate: Vigorous.

Branching habit: Basal rosettes of leaves from rhizomes.

Foliage description:

- *Leaf shape*.—Spatulate.
- *Leaf division*.—Simple.
- *Leaf base*.—Truncate to base of rhizome.
- *Leaf apex*.—Broadly acute to rounded, sometimes slightly notched.
- *Leaf venation*.—Pinnate, matches surface colors.
- *Leaf margins*.—Entire to slightly undulate.
- *Leaf attachment and arrangement*.—Whorled, held in in clumps.
- *Leaf orientation*.—Upright to slightly outward.
- *Leaf surface*.—Very finely puberulent on upper surface, slightly rough to the touch, both surfaces glossy, lower surface glabrous.
- *Leaf color*.—Young upper surface; 137A and NN137A and heavily suffused with N187A, base 144A, young lower surface; N148A, maturing upper surface; 139A, flushed with 202A and 187A, maturing lower surface 139A, mature and winter upper surface; 138A, slightly flushed with 187A, mature and winter lower surface 138A.
- *Leaf size*.—Average of 6 cm in length, 1.5 cm in width.
- *Leaf quantity*.—Average of 40 in a clump 5 cm in diameter.
- *Leaf attachment*.—Sessile.

Flower description:

- *Inflorescence typel*.—Verticillaster, terminal spike, individual flowers in clusters held in leaf-axils.
- *Inflorescence size*.—An average of 12 cm in height and 4 cm in width.
- *Inflorescence number*.—70 to 90 as a fully mature plant grown in a 1-gallon container.
- *Lastingness of inflorescence*.—10 to 14 days, self-cleaning.
- *Flower type*.—Labiate.
- *Flower number*.—Average of 60 per inflorescence.
- *Flower fragrance*.—Very faint, pleasant.

*Flower buds*.—Oblanceolate in shape, average of 5 mm in length and 2 mm in diameter, color; immature bud 145A, mature bud 97C, immature calyx N187A, surface matte and densely covered with soft woolly pubescence up to 1 mm in length and 92D in color.

*Flower size*.—Average of 1.4 cm in depth, 5 mm in diameter, throat 3 mm in diameter, tube 3 mm in length and 1 mm in diameter.

*Peduncles*.—An average of 9 cm in length, 3 mm in diameter, vertical to curved at a 45° angle, moderately strong, color; 144A, surface is glossy and densely covered with soft woolly pubescent hairs up to 1 mm in length and matching surface color.

*Calyx*.—Rotate and tubular in shape, 2 mm in length and diameter.

*Sepals*.—5, 50% fused at base, average of 1 mm in length, 0.5 mm in width, ovate in shape, apex acute, entire margins, surface is covered with long woolly hairs matching surface color, color inner and outer surface 144C, tips 144A.

*Petals*.—50% of petals fused into tube, upper central lobe; notched, average of 6 mm in length, 4 mm in width, blunt and rounded in shape, obtuse apex, entire margins, not undulate, upper and lower surface glabrous, slightly glossy and velvety, color; upper surface when opening and fully open 90A, streaked in middle 92C, lower surface when opening and fully open 97C, outer lobes; 2, average of 2 mm in length and width, oblanceolate in shape, apex is obtuse, entire margins, no undulation, upper and lower surface glabrous and slightly glossy, color; upper surface when opening and fully open 90A, streaked in middle 92C, lower surface when opening and fully open 97C, flower throat and tube; outer surface covered with woolly soft pubescence, inner surface is smooth and glabrous, color; inner and outer surface when opening and fully open 97D.

Reproductive organs:

*Pistils*.—1, style; 5 mm in length, 92D in color, stigma; non-distinguishable, ovary; oblong, 1 mm in length and width, NN155D in color.

*Stamens*.—4, filament; implanted into flower tube, average of 3 mm in length, 92D in color, anthers; minute, 0.05 mm in diameter, 203A in color, pollen; very low in quantity, 9C in color.

*Fruit*.—Fruit and seed production has not been observed to date.

It is claimed:

1. A new and distinct variety of *Ajuga* plant named 'Nobnig' as described and illustrated herein.

* * * * *